(12) United States Patent
Dawson et al.

(10) Patent No.: US 10,751,185 B2
(45) Date of Patent: Aug. 25, 2020

(54) TREATMENT OF SKELETAL VOIDS WITH IMPLANTABLE SUBSTRATE HYDRATED WITH BONE MARROW CONCENTRATE

(71) Applicant: SpineSmith Partners, L.P., Austin, TX (US)

(72) Inventors: Eileen Dawson, Austin, TX (US); Kevin Dunworth, Austin, TX (US); Theodore Sand, Austin, TX (US); Matthew Murphy, Austin, TX (US); John B. Rossman, Austin, TX (US); Melissa Samano, Austin, TX (US); Richard Suzuki, Austin, TX (US); Kathryn Moncivais, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 199 days.

(21) Appl. No.: 15/168,199

(22) Filed: May 30, 2016

(65) Prior Publication Data
US 2016/0270920 A1 Sep. 22, 2016

Related U.S. Application Data

(63) Continuation-in-part of application No. 14/921,826, filed on Oct. 23, 2015, now Pat. No. 10,183,095.

(60) Provisional application No. 62/067,815, filed on Oct. 23, 2014.

(51) Int. Cl.
*A61F 2/28* (2006.01)
*A61F 2/44* (2006.01)
(Continued)

(52) U.S. Cl.
CPC .......... *A61F 2/2846* (2013.01); *A61F 2/4465* (2013.01); *A61F 2/4601* (2013.01); (Continued)

(58) Field of Classification Search
CPC .... A61F 2/2846; A61F 2/4465; A61F 2/4601; A61F 2002/2817; A61F 2002/2825; A61F 2002/285; A61F 2002/30062; A61F 2002/30622; A61F 2002/4475; A61L 27/12; A61L 27/20; A61L 27/22; A61L 27/222; A61L 27/225; A61L 27/227; A61L 27/24; A61L 27/3834; A61L 27/3847;
(Continued)

(56) References Cited

U.S. PATENT DOCUMENTS

| | | | |
|---|---|---|---|
| 10,064,737 B2 * | 9/2018 | Tsai | A61F 2/4455 |
| 2001/0039456 A1 * | 11/2001 | Boyer, II | B29C 43/006 623/23.52 |

(Continued)

*Primary Examiner* — Tessa M Matthews
(74) *Attorney, Agent, or Firm* — Winstead PC

(57) ABSTRACT

The invention is directed to a bone void filler comprising a scaffold or matrix. The scaffold or matrix may include a porous inorganic matrix component and/or a 3D-printed implantable device. The bone void filler may include a cellular component containing cells, some of which are capable of making extracellular matrix resembling native bone tissue. The bone void filler may include an organic matrix, such as, an organic biopolymer that aids in cell retention and renders the scaffold or matrix moldable. The bone void filler may include growth factors and/or cytokines. The bone void filler may include a clotting agent.

19 Claims, 6 Drawing Sheets

(51) Int. Cl.
    *A61L 27/56* (2006.01)
    *A61F 2/30* (2006.01)
    *A61F 2/46* (2006.01)
    *A61L 27/38* (2006.01)
    *A61L 27/22* (2006.01)
    *A61L 27/20* (2006.01)
    *A61L 27/24* (2006.01)
    *A61L 27/12* (2006.01)

(52) U.S. Cl.
    CPC ............... *A61L 27/12* (2013.01); *A61L 27/20* (2013.01); *A61L 27/22* (2013.01); *A61L 27/222* (2013.01); *A61L 27/225* (2013.01); *A61L 27/227* (2013.01); *A61L 27/24* (2013.01); *A61L 27/3834* (2013.01); *A61L 27/3847* (2013.01); *A61L 27/56* (2013.01); *A61F 2002/285* (2013.01); *A61F 2002/2817* (2013.01); *A61F 2002/2825* (2013.01); *A61F 2002/30062* (2013.01); *A61F 2002/30593* (2013.01); *A61F 2002/30622* (2013.01); *A61L 2300/412* (2013.01); *A61L 2300/414* (2013.01); *A61L 2430/02* (2013.01)

(58) Field of Classification Search
    CPC ............... A61L 27/56; A61L 2300/412; A61L 2300/414; A61L 2430/02
    See application file for complete search history.

(56) References Cited

U.S. PATENT DOCUMENTS

| | | | |
|---|---|---|---|
| 2003/0078668 A1* | 4/2003 | Michelson | A61B 17/7059 623/17.16 |
| 2005/0112397 A1* | 5/2005 | Rolfe | A61B 17/8605 428/593 |
| 2010/0185289 A1* | 7/2010 | Kirwan | A61F 2/4455 623/17.11 |
| 2011/0040334 A1* | 2/2011 | Kaes | A61F 2/28 606/279 |
| 2012/0185047 A1* | 7/2012 | Wooley | A61F 2/4465 623/17.16 |
| 2012/0191188 A1* | 7/2012 | Huang | A61F 2/447 623/17.11 |
| 2012/0277870 A1* | 11/2012 | Wolters | A61F 2/447 623/17.16 |
| 2013/0116793 A1* | 5/2013 | Kloss | A61F 2/4455 623/17.16 |
| 2014/0012384 A1* | 1/2014 | Kana | A61F 2/4465 623/17.16 |
| 2014/0107786 A1* | 4/2014 | Geisler | A61F 2/30965 623/17.16 |
| 2014/0288649 A1* | 9/2014 | Hunt | A61F 2/447 623/16.11 |
| 2015/0010607 A1* | 1/2015 | Francis | A61K 35/28 424/422 |

* cited by examiner

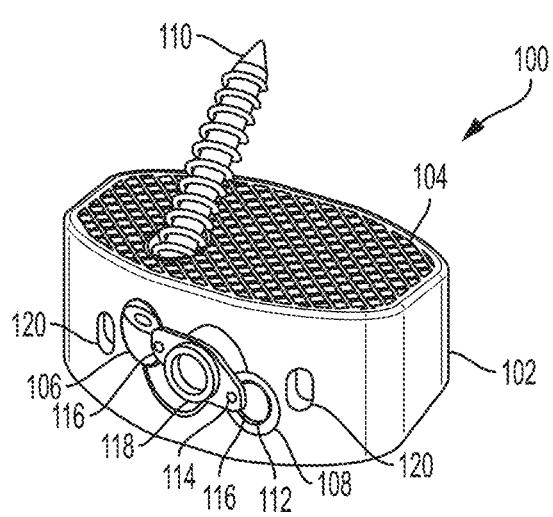
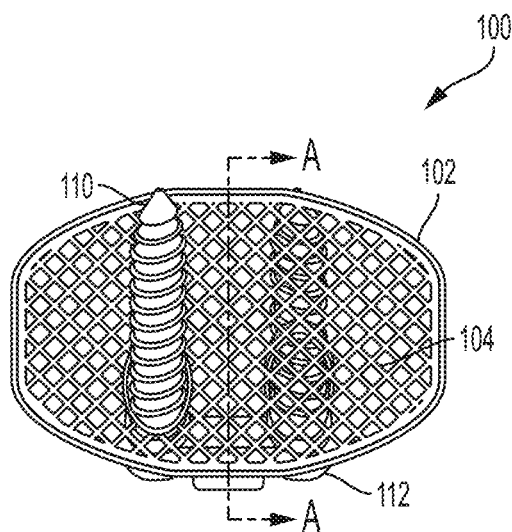
FIG. 5                FIG. 6
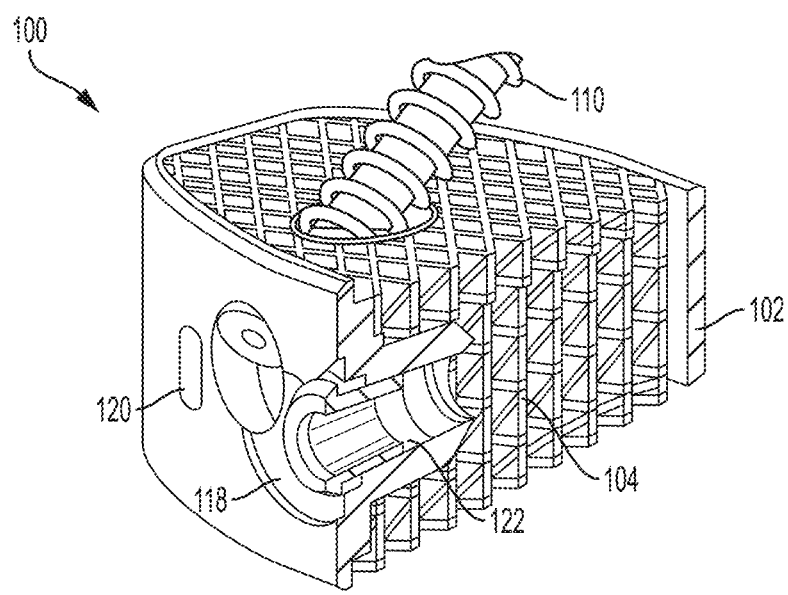
FIG. 7

TREATMENT OF SKELETAL VOIDS WITH IMPLANTABLE SUBSTRATE HYDRATED WITH BONE MARROW CONCENTRATE

CROSS-REFERENCES TO RELATED APPLICATIONS

This application is a Continuation-in-Part of U.S. patent application Ser. No. 14/921,826, filed on Oct. 23, 2015, which claims priority to U.S. Provisional Patent Application No. 62/067,815 filed Oct. 23, 2014. U.S. patent application Ser. No. 14/921,826 and U.S. Provisional Patent Application No. 62/067,815 are each incorporated herein by reference in its entirety as if fully set forth herein.

TECHNICAL FIELD

The claimed invention relates generally to medical devices and procedures and more particularly to devices and methods for treating defects in the tissue of a living being.

BACKGROUND OF THE INVENTION

To better treat our aging population, physicians are looking for new and better products and methods to enhance the body's own mechanism to produce rapid healing of musculoskeletal injuries and degenerative diseases. Treatment of these defects has traditionally relied upon the natural ability of these types of tissue to repair themselves. In many instances the body is unable to repair such defects in a reasonable time, if at all. Advances in biomaterials has allowed for the creation of devices to facilitate wound healing in both bone and soft tissues defects and injuries. Such devices are used in tissue regeneration as tissue (e.g., bone) graft scaffolds, for use in trauma and spinal applications, and for the delivery of drugs and growth factors.

Bone and soft tissue repair is necessary to treat a variety of medical (e.g., orthopedic) conditions. For example, when hard tissue, such as bone, is damaged as a result of disease or injury, it is often necessary to provide an implant or graft to augment the damaged bone during the healing process to prevent further damage and stimulate repair. Such implants may take many forms (e.g. plugs, putties, rods, dowels, wedges, screws, plates, etc.) which are placed into the tissue. Typically, such implants can be rigid, flexible, deformable, or flowable and can be prepared in a variety of shapes and sizes. For rigid implants (e.g., bone screws), the defect site is typically preconditioned by forming a depression, channel, or other feature (e.g., pre-tapped hole) therein in preparation for the application of the implant. For non-rigid structural repair materials (e.g. putties and pastes) to be conveniently used, they must be capable of being formed into a variety of complex shapes to fit the contours of the repair site. An accurately configured implant that substantially fills the defect site will enhance the integration of natural bone and tissue to provide better healing over time. For example, when repairing defects in bone, intimate load carrying contact often is desired between the natural bone and the bone substitute material to promote bone remodeling and regeneration leading to incorporation of the graft by host bone.

Current bone graft materials include autografts (the use of bone from the patient), allografts (the use of cadaver bone), and a variety of other artificial or synthetic bone substitute materials. Autografts are typically comprised of cancellous bone and/or cortical bone. Cancellous bone grafts essentially provide minimal structural integrity. Bone strength increases as the implant incorporates surrounding cells and new bone is deposited. For cortical bone, the graft initially provides some structural strength. However, as the graft is incorporated by the host bone, nonviable bone is removed by resorption, significantly reducing the strength of the graft. The use of autograft bone may result in severe patient pain and other complications at the harvest site, and there are limitations to the amount of autograft bone that can be harvested from the patient. Allografts are similar to autografts in that they are comprised of cancellous and/or cortical bone with greater quantities and sizes being typically available. Disadvantages of allografts include limited supplies of materials and the potential for transmission of disease. The disadvantages of the existing products creates a need for a better devices and methods for treating defects in the tissue of a living being.

After blood, bone is the most commonly transplanted tissue and autografts/allografts are used in approximately 2.2 million orthopedic procedures annually. However, the usage of autograft and allograft materials as bone substitutes carries a number of possible complications. In autografts, considered the gold standard in bone substitutes, bone graft material is limited to patient sample availability, and thus is not a suitable candidate material for larger bone defects. For example, an iliac crest bone graft involves a surgical procedure to recover cortical/cancellous bone from the patient's iliac crest. Such procedures are associated with chronic pain at the site of graft harvest and a limited volume of autograft, since the iliac crest usually doesn't completely regenerate after harvesting. Issues of donor site morbidity have been reported. Allografts, although more widely available and without the same complications associated with sample harvesting, can result in other complications to the patient, notably disease transmission. Over 96% of FDA recalled allograft tissues were musculoskeletal allografts as a result of contamination, improper donor evaluation, and recipient infections. Additionally, allograft materials have been shown to lack the osteoinductive capacities of autograft samples. Therefore, there exists a need for the development of a synthetic alternative for bone grafts. When considering choices for this type of tissue replacement, a number of key material parameters need to be evaluated. The material would need to be non-toxic, non-immunogenic, capable of bonding with the host bone, capable of supporting in-growth of new bone into the graft, and biodegradable. The graft itself would need also to have adequate surface area contact between the graft and recipient site. While this could be accomplished by modifying the graft site with a reamer, burr or bone shaver, use of these instruments can cause heat generation, which may result in tissue necrosis. In some embodiments, a device and process in which the substrate closely mimics natural bone tissue is deployed in such a manner as to take into consideration the biology of tissue remodeling at the site of injury.

Wound healing in response to injury involves the coordination of a large number of complex cellular and molecular events within the body. This response is defined by the need for cells to respond to signals from the pathologic site, mobilize and migrate to the site of injury, secrete trophic factors, possibly proliferate, promote formation of blood vessels, and, eventually, promote synthesis of extracellular matrix to restore the structure and function of the damaged tissue. These cellular processes are driven by a wide variety of proteins, growth factors, and cytokines that act to control cellular functions. The contribution of cells is often overlooked in biomaterials-based approaches for orthopedic healing, but ultimately cells present at the treatment site, whether transplanted or recruited endogenously, are responsible for new tissue generation and remodeling. It has recently been reported that many FDA-cleared biomaterials for bone healing are not efficient at retaining cells and, in many instances, were cytotoxic and had pH values less than 7 or greater than 10 when reconstituted. Materials that were not easily soluble (allograft bone and calcium phosphates) were most successful at retaining bone marrow MSCs and inducing osteogenic gene expression in an in vitro simulation of surgical graft preparation.

In addition to the effects of materials on cells, the source and number of cells must be considered. Many in vivo studies combine biomaterials with culture-expanded autologous or allogeneic cells as an implantable graft. Although this is convenient to standardize "doses" of therapeutic agents and seemingly control one variable of the regenerative paradigm, the clinical translation of this lab-oriented approach raises potential regulatory issues with the Food and Drug Administration (FDA) and other agencies. The usage of autologous cells at the point-of-care is an appealing alternative with fewer regulatory requirements and a decreased risk of cell contamination or rejection. A growing amount of data has suggested differences in clinical outcomes in non-union fracture, rotator cuff tear, avascular necrosis, and other orthopedic injuries based on the concentration of MSCs present in bone marrow. The influence of concentration of non-cultured, freshly obtained MSCs on bone formation when combined with HA granular particles is unknown.

Autologous bone grafts are successful because they are comprised of a number of components necessary for tissue regeneration: progenitor cells from the bone marrow, an extracellular matrix to support cellular growth, and osteogenic proteins and growth factors. In order to successfully create new tissue, all three factors need to be integrated, combining both autologous and synthetic materials in order to create an implantable device that elicits normal tissue restoration and achieves full repair.

3D printed orthopedic devices and implants made of inorganic materials and manufactured using 3D-printing technology have been made. However, these devices and implants lack appropriate surface features and internal structure to optimally support bony in-growth.

In the traditional approach, the use of bone void fillers, granular inorganic materials, such as, for example, tricalcium phosphate, and hydroxyapatite, are formed into blocks or particles of varying porosities. The porosities and voids are subject to a wide range of dimensional outcomes (e.g., see FIG. 1). Due to the varying levels of porosity, among other features, block forms made of these materials typically may not be strong enough to function as structural implants.

Thus, there is a need to create non-human, donor-derived substrates to support the repair, reconstruction, and replacement of damaged or diseased tissues. These devices can be composed of a variety of materials including titanium. The inventive concept addresses the inadequacies of current devices by offering a composition, method of use, and means of manufacture to provide for an optimal microenvironment to promote bony growth and repair.

SUMMARY OF THE INVENTION

Critically-sized bony defects arise from traumatic injury, tumor resection, autologous bone graft harvesting, and surgical procedures including spinal fusion. Autografts, considered the gold standard in bone substitutes, are impractical for use in larger defects as graft size would be limited to patient sample availability. Additionally, pain and local donor site morbidity are commonly reported at the site of graft harvesting. Autografts are successful in defect treatment because they combine a number of key aspects necessary for tissue growth. Successful bone regeneration requires contributions from all aspects of the "tissue engineering paradigm": cells, scaffolds, and biochemical/biomechanical signals.

Significant research has investigated various biomaterials and scaffolding techniques with osteoconductive or osteoinductive properties. Among these biomaterials is hydroxyapatite (HA), the primary form of calcium phosphate comprising the inorganic portion of bone, which has consistently demonstrated an ability to promote bone growth in vivo. Most commonly, monolithic scaffolds are utilized, usually conforming to the pre-determined shape of defects created in animal models. In clinical application, this type of scaffold would be impractical. An implanted scaffold would need to fill the entire volume of the defect, but having a pre-formed scaffold would limit its application to defects of specific sizes or require the physician to modify the graft or the graft site. This modification could have deleterious effects to the patient in that use of a reamer or burr to change the defect site can cause heat generation potentially resulting in local tissue necrosis. Ultimately, a moldable formulation may reduce surgical time as well as avoid additional bone loss or trauma to the surrounding tissue area. It would therefore be advantageous for the scaffolding material to be moldable to irregular geometries present in most clinical cases in order to completely fill the defect and bridge the native bone.

There are, however, a number of physical characteristics of bone that would need to be retained. The inclusion of porosity in scaffolds cannot be understated, as there is typically a correlation between the extent and interconnectivity of pores and the scaffold's ability to regenerate bone. This characteristic can be achieved with ceramics by employing a granular or microparticle formulation. This approach has been validated in limited studies without specific tailoring of granule porosity or surface area nor through characterization of the cellular component of the graft.

An embodiment of the invention is directed to a filler for repair or regeneration of bone tissue. The filler incorporates the use of a scaffold matrix that comprises a porous granule, a cellular component, and an organic biopolymer. Other embodiments may include a growth factor and/or cytokine component.

An embodiment of the invention includes using a growth factor comprising at least one of vascular endothelial growth factor and plate-derived growth factor. In other embodiments, a cytokine is also added to the filler.

An embodiment of the invention includes using a growth factor comprising an autologous growth factor that has been concentrated from a biological fluid. In some embodiments, the concentrated biological fluid comprises at least one of a platelet poor fraction of blood and/or bone marrow.

An embodiment of the invention includes a porous granule that has a porosity between about 50% and about 95% by volume. In another embodiment, the porous granule comprises a porosity between about 3% and about 15% by volume.

An embodiment of the invention uses a porous granule that is formed from a composition selected from the group consisting of calcium phosphate, mono calcium phosphate, tricalcium phosphate, tetra calcium phosphate, octacalcium phosphate, hydroxyapatite, carbonate apatite, fluoro apatite.

In another embodiment, the porous granule also comprises one or more of silicon, strontium, magnesium, or a sinterable metal powder like titanium.

An embodiment of the invention uses an organic biopolymer comprising one or more of collagen, gelatin, fibrinogen, vitronectin, fibronectin, albumin, peptides, chitin, alginate, cellulose, carboxymethycellulose.

An embodiment of the invention uses a cellular component comprising autologous bone marrow. In some embodiments, the autologous bone marrow is filtered to remove at least one of the red blood cells and extracellular components. An embodiment of the invention uses a cellular component comprising autologous adipose tissue. In some embodiments, the autologous adipose tissue comprises progenitor cells. An embodiment of the invention uses a cellular component comprising concentrated autologous progenitor cells. In some embodiments, the cellular component comprises concentrated allogeneic progenitor cells.

An embodiment of the invention includes the use of a clotting agent.

An embodiment of the invention is directed to a method that incorporates the use of concentrated autologous cells, including progenitor cells, which are known to support the body's natural response to injury and promote bone healing, delivered directly to the site of injury while seeded on a biomimetic substrate. In this way, the highest concentration of progenitor cells is delivered to the site of injury in combination with an osteogenic implant in the smallest volume possible, minimizing the implantation space while maximizing the regenerative capabilities of the implant. This method will be applicable for any defect within the body. This will include defects within the skeletal system including spine, pelvis, and extremities.

An embodiment of the invention is directed to a 3D-printed titanium implant that includes features that are conducive to the attachment and proliferation of cells commonly found in the body, especially those found in the bone marrow and adipose tissue. The cells can include hematopoietic stem cells, mesenchymal stem cells and other progenitor cells that have been shown to play an important role in creating a biologically-supportive microenvironment. The inventive device will contain portions that resemble what is typically referred to as "cancellous" bone, as well as "cortical" bone. These zones will be connected by elements that render the entire implant capable of being weight-bearing, making the implant suitable for use as a bone replacement or bone spacer. Typical sites of use would be in the spine or extremities when a fusion of adjacent bony structures is desirable.

In one embodiment, the 3D-printed titanium implant is contacted with a patient's own autologous cell preparation, typically obtained from the patient's concentrated bone marrow or adipose tissue. In a typical embodiment, the cell preparation fills internal pores of the device prior to being placed at the site of pathology. In one embodiment, the 3D-printed implantable device includes features that facilitate attachment of various cells found in bone marrow (or other cell-containing preparation) to pores within a mesh-like structure of the 3D-printed implantable device, which subsequently fosters continued viability of the cells over an extended period of time. The pores of the 3D-printed implantable device can also facilitate various cell types to expand in number within the microenvironment provided by the mesh-like structure of the 3D-printed implantable device. In this regard, the 3D-printed implantable device can be described as having features similar to that of a substrate made of, such as, for example, hydroxyapatite, and thus also can be considered as a "substrate" and not just an implant.

In a typical embodiment, the 3D-printed implantable device is made by the use of sinterable materials, such as, for example, titanium and the like, that can be dispensed by 3D-printing technology. The design of the 3D-printed implantable device is optimized for creating a microenvironment that is conducive to the attachment and proliferation of various types of progenitor cells. In a typical embodiment, the 3D-printed implantable device includes features that create a porosity that mimics pore sizes, connectedness, and pore-size distribution commonly found in cancellous bone and/or cortical bone. In addition to control over the physical dimensions of the 3D-printed implantable device, including pores, tunnels, channels, and other physical elements of the 3D-printed implantable device, a surface texture of the 3D-printed implantable device can also be adjusted or modified to enhance the attachment of cells critical to the production of bony tissues.

In a typical embodiment, the 3D-printed implantable device possesses certain physical features that facilitate its insertion into a site of pathology. These features enable secure attachment of implanting tools for handling and positioning the device during deployment at the site of pathology. A further aspect of the design of the 3D-printed implantable device accommodates in-situ loading of channels, tunnels and pores of the 3D-printed implantable device with biological preparations, including autologous or allogeneic proteins, fluids, and cells. This dynamic loading feature will facilitate the optimal loading of the 3D-printed implantable device, further enhancing the formation of bony tissues.

BRIEF DESCRIPTION OF THE DRAWINGS

FIG. 5 is an isometric view of a 3D-printed implantable device;

FIG. 6 is a top view of the 3D-printed implantable device of FIG. 5;

FIG. 7 is a vertical-sectioned view of the 3D-printed implantable device of FIG. 5;

DETAILED DESCRIPTION OF EXEMPLARY EMBODIMENTS

Figure 1:
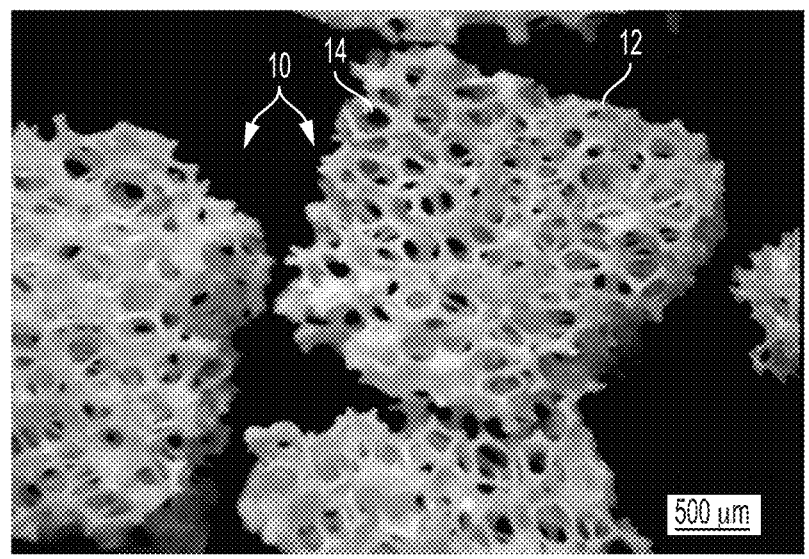
FIG. 1 is a scanning electron microscope (SEM) image of porous hydroxyapatite granules.

The extracellular matrix of hard tissues is composed of two distinct phases, an organic phase and an inorganic phase. The inorganic portion of bone is comprised mainly of hydroxyapatite while the organic phase is primarily comprised of type I collagen and smaller amounts of other proteins. Structurally, although hard, bone is a porous material, with porosities of 50-90% in trabecular bone and 3-12% in cortical bone. By providing a substrate containing osteogenic progenitor cells, in combination with the biological binding cues from the organic phase as well as some of the mechanical rigidity seen in the inorganic phase, it may be possible to produce a fully functional device capable of supporting osteogenic differentiation as well as new bone growth. In certain embodiments, the organic phase contains growth factors and/or proteins that aid in the repair process.

Calcium phosphate based materials are a popular synthetic bone graft material because they have been shown to demonstrate an ability to incorporate within natural bone, as well as have osteoconductive properties. Two of the most widely researched materials of this type are hydroxyapatite and β-tricalcium phosphate (β-TCP). Hydroxyapatite has high biocompatibility, good bioaffinity, has been shown to stimulate osteoconduction, and can be further integrated/replaced by the host bone after implantation. Porosity of hydroxyapatite has been shown to be incredibly important in osteogenic differentiation on both a micro and macro level of organization. In combination with rigid plating to provide mechanical support, hydroxyapatite materials have demonstrated an ability to fully incorporate and patients reported significant decreases in pain. One limitation in this type of therapy is that the scaffold must have a high surface area and a high degree of surface contact with the bone for the implantation to be successful. Moldable formulations may be preferred as compared to rigid scaffolds in that they can take the shape of any treatment space. By the using moldable substrates, a surgeon would not need to fit the surgical site around the implant or modify the implant to fit the target space. Ultimately, this will reduce surgical time, as well as avoid additional bone loss or trauma to the surrounding tissue area.

Because cells need specific substrates to drive differentiation, particle formulations combined with a delivery vehicle have been investigated. By utilizing a microparticle based system, it is possible to capitalize on the osteogenic properties of the scaffold material, but use it in a moldable formulation. Additionally, particulate based formulations have a much higher surface area, which may alter the degradation rates of the materials resulting in faster implant incorporation. By including a matrix system to hold the microparticles together, it is possible to add not only better handling properties, but also increase cell affinity/bioactivity of the inventive implant. Further, the particles can be used to incorporate an extra dimension of porosity in that the spaces between tightly packed particles can be used to create interconnected pores throughout the implant.

Collagen (type I) is the most abundant extracellular protein of bone, the structure of which has been shown to be important for cell attachment, proliferation and differentiation. Gelatin, a derivative of collagen, is biocompatible and biodegradable and has been widely investigated as a carrier material for other biological agents in bone applications. Further, incorporation of gelatin has been shown to increase cell adhesion as well as proliferation of cells. This effect has been demonstrated in a variety of ways, most notably in simple coating procedures. When combined with hydroxyapatite particles, particles incorporating gelatin showed significantly enhanced cell binding as compared to hydroxyapatite particles alone. Other naturally derived biopolymers have been investigated as scaffold-based materials including alginate, chitosan, and fibrin.

With inclusion of autologous, patient-derived factors, including cells and proteins, the full therapeutic potential of this type of device can be realized. While hydrating implantable materials with bone marrow aspirate has been investigated, the effects of cell and protein concentrations often are not considered. In critical-sized, long bone non-unions, a greater than physiological concentration of progenitor cells was shown to promote bony union. Incorporating autologous growth factors and proteins within the matrix material will provide additional support to amplify the beneficial effects of the cells. Growth factors can act to aid in tissue repair in a number of ways. One of the essential steps in wound repair is the generation of new blood vessels in order to ensure the delivery of nutrients, as well as facilitate removal of waste products and debris. Vascular endothelial growth factor ("VEGF"), for example, is a potent angiogenic factor that is capable of stimulating endothelial cell migration and activation, as well as angiogenesis. Further, VEGF has been shown to have a significant role in bone repair. Plate-derived growth factor ("PDGF"), another growth factor found in plasma, is a potent mitogenic and chemotactic factor for a variety of cells, including fibroblasts and smooth muscle cells. The presence of growth factors and cytokines within the matrix will encourage recruitment of additional host cells within the defect and help to further reduce the time necessary for tissue formation and repair of the pathology.

The inventive process and methods are an improvement on the art of using a bone void filler in that it combines all necessary factors in the healing cascade in a concentrated manner, maximizing the regenerative capabilities of the implanted device. The scaffold material offers the ability to not only offer a substrate that the concentrated cells will preferentially bind to, but also be adsorbed as new tissue is formed, allowing for complete repair of tissue. The addition of autologous growth factors will recruit other necessary cells from the surrounding host tissue, thus further augmenting the healing cascade.

DESCRIPTION OF EXEMPLARY EMBODIMENTS

A cellular component is defined as a fluid containing cells, some of which are known to be progenitors of bone-forming cells that are capable of making extracellular matrix resembling native bone tissue, with a composition that is not naturally occurring in the body. Examples of the inventive device include the following:
  a. Autologous bone marrow concentrated and/or filtered to remove red blood cells, while retaining growth factors and mononuclear cells at a concentration greater than 1.1×.
  b. Autologous bone marrow concentrated and/or filtered to remove all other extracellular components at a concentration greater than 1.1×.
  c. Autologous adipose tissue filtered, enzymatically digested, and/or concentrated to isolate known progenitor cells at a concentration greater than 1.1× natural cell concentration.
  d. Autologous progenitor cells that have been isolated and expanded ex vivo to be 1.1× or more the concentration of the cells found in native tissue.
  e. Allogeneic progenitor cells that are 1.1× or more the concentration of the cells found in native tissue.
  f. Any combination of the above.

The inorganic matrix part of the scaffold material is defined as a porous particle such that it mimics the inorganic portion of natural bony tissue. Examples include the following:
  a. The inventive matrix can be formulated in a variety of formats, including a granule form, a powder form, a strip form and a block form.

b. Porosity will mimic that found in bone ranging from 50-95% or 3-15% porosity.
c. Granule composition may include calcium phosphate, mono calcium phosphate, tricalcium phosphate, tetra calcium phosphate, octacalcium phosphate, hydroxyapatite, carbonate apatite, fluoro apatite, or any combination thereof.
d. The granule composition may also contain materials to mimic the ionic characteristics of bone, this may include (but is not limited to): silicon, strontium, or magnesium.

The organic matrix part of the scaffold material is defined as an organic biopolymer either natural or synthetic that would act to aid in cell retention as well as render the scaffold in a moldable format. The organic matrix can be made up of a single biopolymer or a mixture of biopolymers. Examples include the following:
a. The biopolymer may be selected from one of the following: collagen, gelatin, fibrinogen, vitronectin, fibronectin, albumin, peptides, chitin, alginate, cellulose, carboxymethycellulose or any combination thereof Growth factors and cytokines are proteins that can be found autologously in blood and bone marrow but delivered in a concentrated form not found naturally within the body. Examples include the following:
a. The growth factors and cytokines can be autologous and concentrated from biological fluids including the platelet poor fraction of blood or bone marrow
b. The growth factors and cytokines can be synthetically derived and incorporated within the scaffold at the discretion of the physician A clotting agent may be added at the discretion of the physician to the device in order to preferentially alter the handling characteristics of the implant.

Animal Study

A total of 33 New Zealand White rabbits were evaluated with both the test and control articles in an animal study. For each rabbit, after anesthetization, bone marrow was harvested from the iliac crest and both the test and predicate device was hydrated (separately) with autologous bone marrow prior to implantation. Samples of the aspirate were retained for further in vitro regenerative analysis. Two drill defects were created in each rabbit (approximately 5-6 mm in diameter and 8-10 mm in length). Once the test and control sites were prepared, the test articles and control articles were implanted into the femoral condyles, each on a separate side. The surgical sites were closed, and the animals were observed daily for 4, 8, and 13 weeks. At 4, 8, and 13 week time points, 10 rabbits were euthanized (at the 13 week time point, all remaining rabbits are euthanized). The test article and control article implant sites as well as the draining lymph nodes were explanted at necropsy. All tissues were fixed in an appropriate fixative.

Characterization and Comparison of HA Components

FIG. 1 is an SEM image of porous hydroxyapatite granules. A granule 10 is shown comprising a scaffold 12. In comparison to other commercially available granules, the scaffold 12 forms a plurality of voids 14 throughout the granule 10. The plurality of voids 14 increases a surface area of the granule 10, which increase facilitates one or more of faster implant incorporation, better handling properties, increased cell affinity/bioactivity, and an overall increase in porosity of in an area of application.

Figure 2:
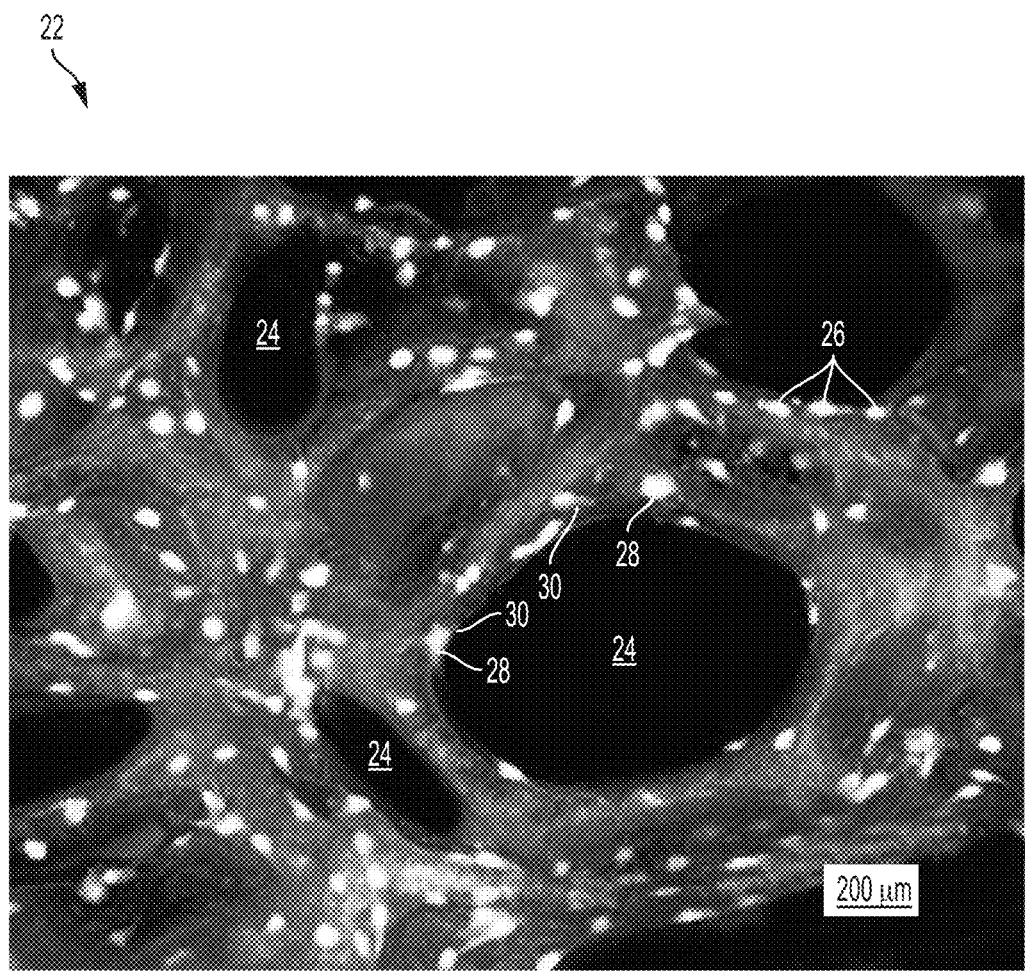
FIG. 2 is an enhanced image showing mesenchymal stem cells proliferated on a porous hydroxyapatite scaffold in vitro.

FIG. 2 is an enhanced image showing mesenchymal stem cells 26 proliferated on a porous hydroxyapatite scaffold 20 in vitro. The porous hydroxyapatite scaffold 20 comprises a structure of a granule 22. The granule 22 may be similar to the granule 10 shown in FIG. 1. The porous hydroxyapatite scaffold 20 comprises a plurality of voids 24, which plurality of voids 24 increases a surface area of the granule 22. Each of the plurality of mesenchymal stem cells 26 comprises a nucleus 28 and fibrillar actin 30. The nuclei 28 are shown in FIG. 2 as white spots disposed on the porous hydroxyapatite scaffold 20. The fibrillar actin 28 is indicated in FIG. 2 by light gray areas surrounding the nuclei 26. The increased surface area provided to the granule 22 by the plurality of voids 24 results in an increased proliferation of mesenchymal stem cells 26 compared to other non-void-containing granules.

Histopathological Analysis

Each implant section was analyzed by a pathologist for local tissue reaction following ISO 10993-6 guidelines, as well as any osteoconductivity, bone growth, and/or bone development within the defect. The test article was compared to the control article. The histopathology data was used to evaluate both local tissue reactions as well as bone formation.

Figure 3:
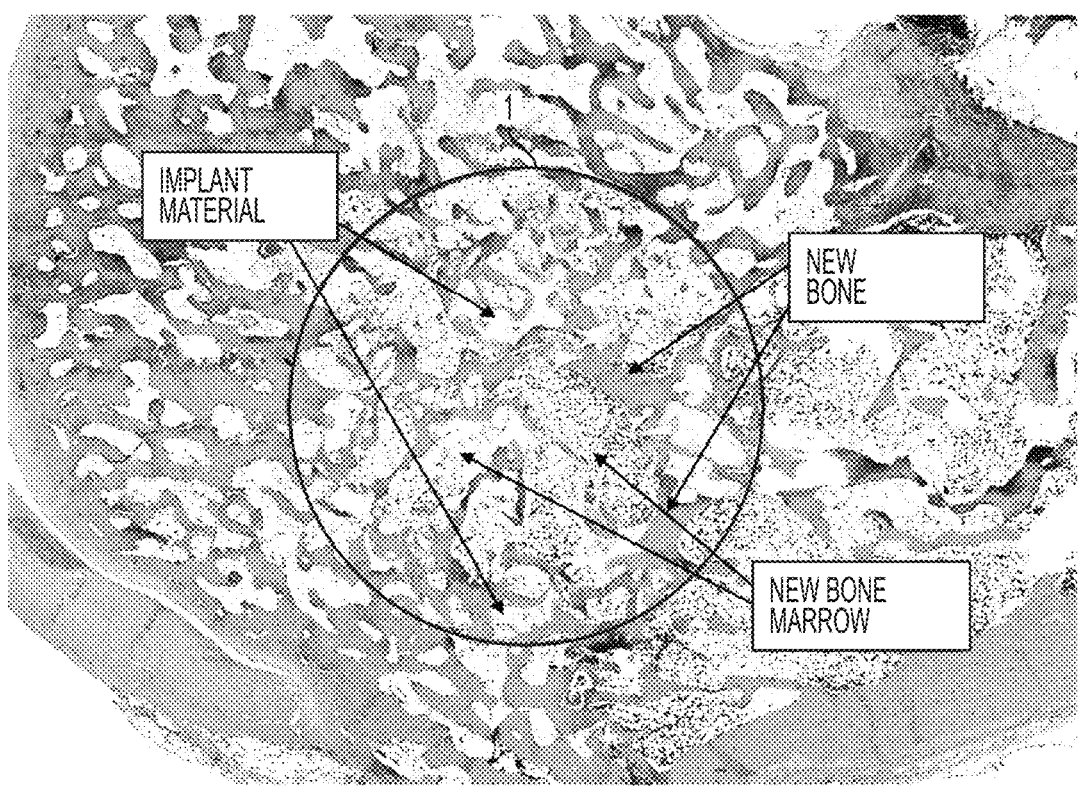
FIG. 3 is an image of a thirteen week test article implant site.
Figure 4:
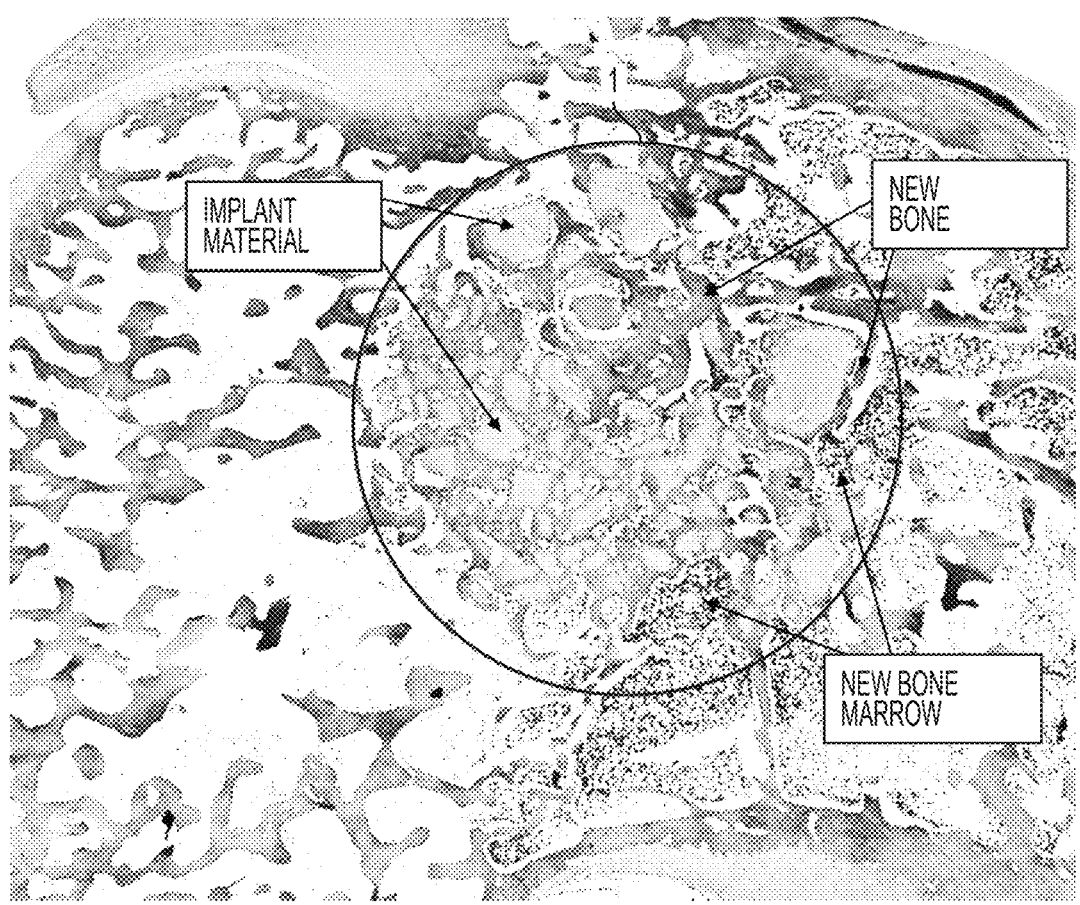
FIG. 4 is an image of a thirteen week control article implant site.

FIGS. 3 and 4 demonstrate histology results for a test article and a control article after a 13 week period, respectively. FIG. 3 shows that implanting porous hydroxyapatite granules was as effective as the predicate control article at promoting new bone development in a defect by having similar tissue responses surrounding the implant sites and within the implant sites as the control article at all durations. Implanting porous hydroxyapatite granules also had faster resorption and increased new bone formation within the implant sites compared to the control article.

High-Resolution MicroCT Bone Imaging

Rabbit condyles were scanned using micro-computer tomography (MicroCT) to visualize new bone formation. The specimens were processed to obtain 3D images in addition to quantitative measurements of bone and material volumes, densities, and trabecular features. All samples were scanned on a high-resolution, volumetric microCT scanner.

Using a documented segmentation process, regions of interest were defined using VHLab software and values were assigned to each voxel in order to be used later for quantitative analysis. Voxel counts were then used to determine the following volume measurements: bone volume (BV), material volume, and total volume (TV) (this would be the total volume of the region of interest). Trabecular morphometric analysis was also performed within the region of interest to determine connectivity density, structure model index, trabecular number, trabecular thickness, trabecular spacing, bone surface, bone surface per bone volume (BS/BV) and mean bone density.

MicroCT analysis of samples where autologous bone marrow aspirate with porous hydroxyapatite granules revealed that the porous hydroxyapatite granules proved to be more effective than implanting autologous bone marrow aspirate with non-porous granules with regard to spurring new bone growth, while also degrading/resorbing more quickly than a control material. New bone formed in samples implanted with porous hydroxyapatite granules had higher mineral density and was less porous and structurally more similar to mature bone. Differences between test and control samples were larger at 13-weeks than 8-weeks for every parameter other than trabecular number and spacing and material volume.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

3D-Printed Implantable Device

The use of 3D-printing technology and, for example, sinterable titanium powder provides a means to create a structurally-stable implant that itself is conducive to supporting the in-growth of bone, by sustaining various populations of cells within its pores during the first few weeks after being implanted in the body. Titanium is known to support the development of bony tissues and is capable of interacting with the emerging bony tissue, but other materials also have similar bone-nurturing properties. Controlling the distribution of pores, the size range of pores and the overall physical geometry of the implants all contribute to a biologically-supportive microenvironment, which in turn promotes the formation of bony tissue. Alternatively, the 3D-printed portion can be combined with a non-3D-printed device, such as, for example, femoral rings from human cadaveric donors or other non-natural structures, to create a composite implant with an optimal biologically-supportive microenvironment and the rigidity of a cortical bone.

Referring generally to FIGS. 5-8, an embodiment of a 3D-printed implantable device 100 is shown. The embodiment shown in FIGS. 5-8 is adapted to be inserted between two vertebrae. In other embodiments, the device 100 may be shaped differently as desired. Referring now to FIG. 5, an isometric view of the 3D-printed implantable device 100 is shown. The device 100 includes an outer body 102 and a mesh 104. In the embodiment shown in FIGS. 5-7, the outer body 102 is generally oval-shaped. In other embodiments, the outer body 102 may take on a variety of other shapes depending upon the intended application of the device 100. In some embodiments, the outer body 102 includes an angled bore 106 and an angled bore 108. Each of the angled bores 106 and 108 extends from the outer body 102 through the mesh 104 and is adapted to receive a screw 110 and a screw 112, respectively. As shown in FIG. 5, the angled bore 106 is angled so that the screw 110 extends out of a top surface of the device 100 and the angled bore 108 is angled so that the screw 112 extends out of a bottom surface of the device 100. In other embodiments, the angle of the bores 106 and 108 can be adjusted as desired. In a typical embodiment, each of the screws 110 and 112 is adapted to screw into an upper and lower vertebra, respectively.

In some embodiments, the device 100 includes an anti-backout plate 114. The anti-backout plate 114 includes two wing portions 116 that can be positioned to cover heads of each of the screws 110 and 112 to prevent the screws 110 and 112 from backing out of the angled bores 106 and 108. In a typical embodiment, the anti-backout plate 114 may be secured to the device 100 via a screw 118. During installation of the device 100, the anti-backout plate 114 may be rotated such that the wing portions 116 do not cover the angled bores 106 and 108 to permit the screws 110 and 112 to be inserted into the angled bores 106 and 108. In other embodiments, additional angled bores may be added as desired. For example, the device 100 could be configured to include two bores that are oriented to direct screws into an upper vertebra and a two bores that are oriented to direct screws into a lower vertebra. In such an embodiment, the anti-backout plate could be configured with four wing portions so that heads of each of the four screws are covered.

In some embodiments, the outer body 102 may also include one or more features that facilitate handling and placing of the device 100. For example, FIG. 5 shows a pair of indentations 120 that facilitate griping of the device 100 by a tool, such as, for example, a pair of pliers and the like, to grip the device 100 to assist with handling and positioning the device 100.

As shown in FIGS. 5-7, the mesh 104 is fills a space within the outer body 102. In a typical embodiment, the mesh 104 is designed to create a plurality of voids within the device 100 that are adapted to receive and hold a material, such as, for example, a filler and/or cell preparation. Because the device 100 is 3D printed, the mesh 104 may take on a variety of shapes and designs depending on the intended application. A porosity of the mesh 104 can be changed based on various design considerations. In some embodiments, the mesh 104 has a porosity of between 50%-95% by volume. As shown in FIGS. 5-8, the mesh 104 comprises a lattice-type design. In a typical embodiment, the device 100 includes features that create a porosity that mimics pore sizes, connectedness, and pore-size distribution commonly found in cancellous bone and/or cortical bone. In addition to control over the physical dimensions of the 3D-printed implantable device, including pores, tunnels, channels, and other physical elements of the 3D-printed implantable device, a surface texture of the 3D-printed implantable device can also be adjusted or modified to enhance the attachment of cells critical to the production of bony tissues.

As shown in FIG. 6, the lattice-type design of the mesh 104 comprises a straight-through design when viewed from the top. Such a design may facilitate tissue growth through the mesh 104 that fuses the two bones or bony ends together. In other embodiments, the mesh 104 may not include a straight-through design when viewed from the top. In such a design, successive layers of the lattice may be offset so that voids are not lined up, or in other embodiments the mesh may be comprised of layers having different patterns that result in voids not aligning with one another.

Referring now to FIG. 7, a sectioned view of the device 100 about line A-A of FIG. 6 is shown. FIG. 7 shows that the outer body 102 is made up of a relatively thin wall compared to an overall width of the device 100. The thickness of the outer body 102 may be changed depending on various design considerations. For example, in some embodiments, it may be desirable to increase the thickness of the outer body 102 to increase the strength of the outer body 102. In some embodiments, the thickness of the outer body 102 may be increased around the various bores of the device 100 to provide additional strength in those areas. FIG. 7 shows that the mesh 104 includes a plurality of voids. In a typical embodiment, the plurality of voids comprises uniformly shaped voids. In other embodiments, the mesh 104 may be designed to include non-uniformly shaped voids. FIG. 7 also shows a bore 122 that extends from the outer body 102 into the mesh 104. The bore 122 is adapted to receive the screw 118 to secure the anti-backout plate 114 to the device 100.

Figure 8:
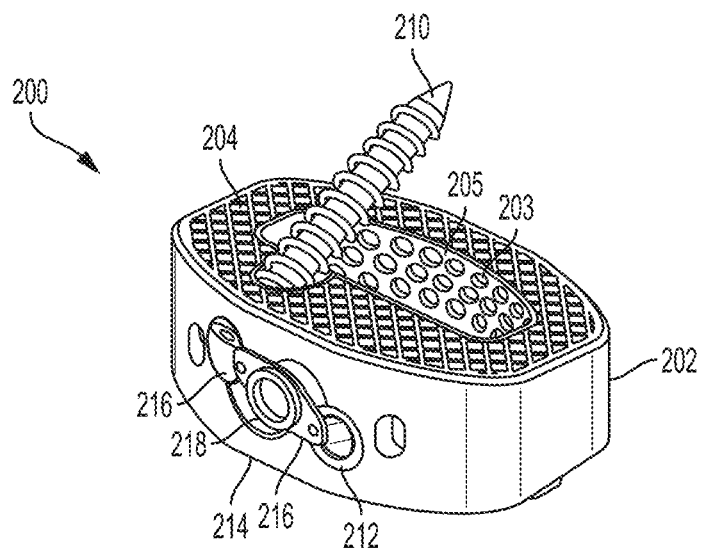
FIG. 8 is an isometric view of a 3D-printed implantable device.

FIG. 8 is an isometric view of a 3D-printed implantable device 200. The device 200 is similar to the device 100, but the device 200 includes a pocket 201 formed through the device 200. The device 200 includes an outer body 202 and a mesh 204. In a typical embodiment, the device 200 includes an angled bore 206 and an angled bore 208. In some embodiments, the device 200 may include additional angled bores as desired. The angled bores 206 and 208 are adapted to receive screws 210 and 212, respectively. The screws 210 and 212 are adapted to secure the device 200 to an upper and a lower vertebra, respectively. In a typical embodiment, the device 200 includes an anti-backout plate 214. The anti-backout plate 214 includes two wing portions 216 that may be positioned over heads of the screws 210 and 212 to prevent the screws 210 and 212 from backing out of the upper and lower vertebrae. In a typical embodiment, the anti-backout plate 214 is secured to the device 200 with a screw 218. In a typical embodiment, the device 200 includes a bore adapted to receive the screw 218 that is similar to the bore 122 of the device 100.

The pocket 201 provides an interior space within the device 200 into which a material, such as, for example, a filler and/or cell preparation, can be inserted. An interior wall 203 of the device 200 surrounds a periphery of the pocket 201. In some embodiments, the interior wall 203 includes one or more perforations 205. The one or more perforations allows for in-growth of the material disposed within the pocket 201 into the mesh 204. A size and shape of the one or more perforations 205 may be varied based on various design considerations. In some embodiments, a filler may be inserted into the mesh 204 and the pocket 201. In some embodiments a first filler may be inserted into the mesh 204 and a second filler may be inserted into the pocket 201.

Figure 9:
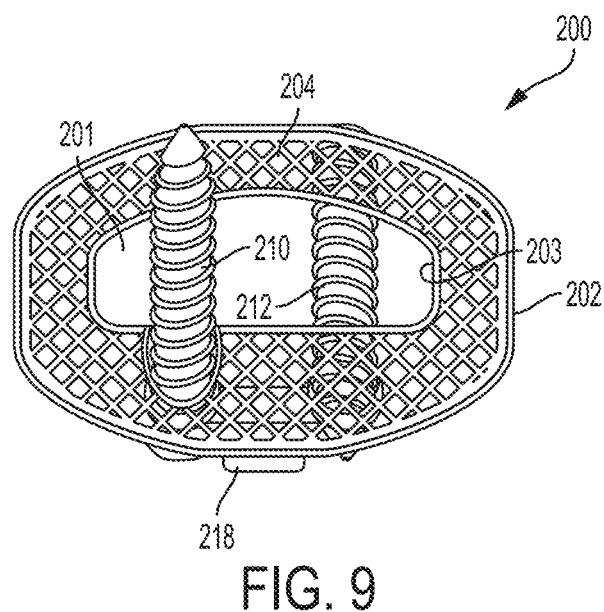
FIG. 9 is a top view of the 3D-printed implantable device of FIG. 9.

FIG. 9 is a top view of the device 200. As shown in FIG. 9, the mesh 204, similar to the mesh 104, comprises a straight-through design when viewed from the top. Such a design may facilitate cell growth between two bones or bony ends resulting in formation of a bony union. In other embodiments, the mesh 204 may not include a straight-through design when viewed from the top. In such a design, successive layers of the lattice may be offset so that voids are not lined up, or in other embodiments the mesh may be comprised of layers having different patterns that result in voids not aligning with one another to create a straight-through design. In some embodiments, the mesh 104 has porosity of between 50%-95% by volume.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

The invention claimed is:

1. A 3D-printed implantable device comprising:
    an outer body that forms a periphery of the 3D-printed implantable device, the outer body comprising a first angled bore and a second angled bore, the first angled bore comprising a first opening that passes through a side of the 3D-printed implantable device and a second opening that passes through a top of the 3D-printed implantable device, and the second angled bore comprising a first opening that passes through the side of the 3D-printed implantable device and a second opening that passes through a bottom of the 3D-printed implantable device;
    a mesh disposed within the outer body;
    a pocket formed through the mesh; and
    an interior wall disposed around a periphery of the pocket, the interior wall comprising a plurality of perforations that permit communication of a material to and from the mesh, wherein the plurality of perforations do not pass through an outer wall of the outer body, wherein the outer wall is substantially solid.

2. The 3D-printed implantable device of claim 1, wherein the mesh comprises lattice-type design.

3. The 3D-printed implantable device of claim 1, wherein the mesh has a porosity of 50-90% by volume.

4. The 3D-printed implantable device of claim 1, wherein the mesh comprises a plurality of voids arranged to create a straight-through design when viewed from the top of the 3D-printed implantable device.

5. The 3D-printed implantable device of claim 1, further comprising an anti-backout plate that comprises:
    a first winged portion that is capable of being positioned over a head of a first screw to prevent the first screw from backing out of the first angled bore; and
    a second winged portion that is capable of being positioned over a head of a second screw to prevent the second screw from backing out of the second angled bore.

6. The 3D-printed implantable device of claim 5, further comprising:
    a screw for securing the anti-backout plate to the 3D-printed implantable device; and
    a bore disposed between the first angled bore and the second angled bore for receiving the screw for securing the anti-backout plate.

7. The 3D-printed implantable device of claim 6, wherein the screw comprises a bore that passes through the screw.

8. The 3D-printed implantable device of claim 1, further comprising an indentation disposed on an outer surface of the outer body that facilitates handling of the 3D-printed implantable device with a tool.

9. The 3D-printed implantable device of claim 1, wherein the first and second angled bores comprise walls that separate the first and second angled bores from the mesh.

10. A system for forming a union between two bones or bony ends, the system comprising:
    an implantable device comprising:
        a substantially solid outer body that forms a periphery of the implantable device, the outer body comprising a first angled bore and a second angled bore, the first angled bore comprising a first opening that passes through a side of the implantable device and a second opening that passes through a top of the implantable device, and the second angled bore comprising a first opening that passes through the side of the implantable device and a second opening that passes through a bottom of the implantable device;
        a 3D-printed mesh disposed within the outer body; and
        a pocket formed through the 3D-printed mesh;
        an interior wall disposed around a periphery of the pocket, the interior wall comprising a perforation that permits communication of a material to and from the 3D-printed mesh; and
        an anti-backout plate and a screw for securing the anti-backout plate to the outer body, the screw comprising a bore that extends through the screw; and
    a filler for repair or regeneration of bone tissue, the filler comprising:
        a cellular component;
        an inorganic component; and
        an organic biopolymer.

11. The system of claim 10, wherein the 3D-printed mesh comprises a lattice-type design.

12. The system of claim 10, wherein the 3D-printed mesh has a porosity of 50-90% by volume.

13. The system of claim 10, wherein the 3D-printed mesh comprises a plurality of voids arranged to create a straight-through design when viewed from the top of the implantable device.

14. The system of claim 10, wherein the anti-backout plate comprises:
   a first winged portion that is capable of being positioned over a head of a first screw to prevent the first screw from backing out of the first angled bore; and
   a second winged portion that is capable of being positioned over a head of a second screw to prevent the second screw from backing out of the second angled bore.

15. The system of claim 10, wherein the outer body and the 3D-printed mesh are both 3D printed as a single component.

16. The system of claim 10, wherein the outer body comprises a femoral ring.

17. The system of claim 10, wherein the filler is placed into the 3D-printed mesh and into the pocket.

18. The system of claim 10, wherein:
   the filler is placed into the 3D-printed mesh;
   a second filler is placed into the pocket; and
   wherein the second filler is a different filler material from the filler in the 3D-printed mesh.

19. The system of claim 10, wherein the first and second angled bores comprise walls that separate the first and second angled bores from the 3D-printed mesh.

* * * * *